(12) United States Patent
Shanbhag et al.

(10) Patent No.: US 10,799,204 B2
(45) Date of Patent: Oct. 13, 2020

(54) SYSTEM AND METHOD FOR EVALUATING MOTION CORRECTION IN DYNAMIC MEDICAL IMAGES

(71) Applicant: GE Precision Healthcare LLC, Wauwatosa, WI (US)

(72) Inventors: Dattesh Dayanand Shanbhag, Bangalore (IN); Venkata Veerendranadh Chebrolu, Bangalore (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 903 days.

(21) Appl. No.: 15/306,616

(22) PCT Filed: Apr. 24, 2015

(86) PCT No.: PCT/US2015/027432
§ 371 (c)(1),
(2) Date: Oct. 25, 2016

(87) PCT Pub. No.: WO2015/164687
PCT Pub. Date: Oct. 29, 2015

(65) Prior Publication Data
US 2017/0042496 A1 Feb. 16, 2017

(30) Foreign Application Priority Data
Apr. 25, 2014 (IN) .......................... 2108/CHE/2014

(51) Int. Cl.
*G06K 9/00* (2006.01)
*A61B 6/00* (2006.01)
(Continued)

(52) U.S. Cl.
CPC .......... *A61B 6/5264* (2013.01); *A61B 5/0035* (2013.01); *A61B 5/0059* (2013.01);
(Continued)

(58) Field of Classification Search
CPC ......... A61B 6/463; A61B 6/527; A61B 6/032; A61B 6/469; A61B 6/037; A61B 6/488;
(Continued)

(56) References Cited

U.S. PATENT DOCUMENTS

2012/0082350 A1 4/2012 Wollenweber
2012/0275676 A1 11/2012 Haacke

FOREIGN PATENT DOCUMENTS

CN 102038502 A 5/2011
CN 102395996 A 3/2012
(Continued)

OTHER PUBLICATIONS

International Search Report and Written Opinion for International Application No. PCT/US2015/027432, dated Jul. 22, 2015, 10 pages.
(Continued)

*Primary Examiner* — Elmer M Chao
(74) *Attorney, Agent, or Firm* — Armstrong Teasdale LLP

(57) ABSTRACT

A method for automated evaluation of motion correction is presented. The method includes identifying one or more regions of interest in each of a plurality of images corresponding to a subject of interest. Furthermore, the method includes selecting valid voxels in each of the one or more regions of interest in each of the plurality of images. The method also includes computing a similarity metric, a dispersion metric, or both the similarity metric and the dispersion metric for each region of interest in each of the plurality of images. Additionally, the method includes generating a similarity map, a dispersion map, or both the similarity map and the dispersion map based on the similarity metrics and the dispersion metrics corresponding to the one or more regions of interest.

23 Claims, 11 Drawing Sheets

(51) Int. Cl.
*A61B 5/055* (2006.01)
*G01R 33/565* (2006.01)
*A61B 5/00* (2006.01)
*G06T 7/00* (2017.01)
*A61B 6/03* (2006.01)
*A61B 8/08* (2006.01)
*G01R 33/56* (2006.01)
*G06K 9/46* (2006.01)
*G06K 9/62* (2006.01)

(52) U.S. Cl.
CPC ............ *A61B 5/055* (2013.01); *A61B 5/7207* (2013.01); *A61B 6/032* (2013.01); *A61B 6/037* (2013.01); *A61B 6/481* (2013.01); *A61B 6/486* (2013.01); *A61B 6/507* (2013.01); *A61B 8/481* (2013.01); *A61B 8/5276* (2013.01); *G01R 33/5601* (2013.01); *G01R 33/56509* (2013.01); *G06K 9/00335* (2013.01); *G06K 9/4671* (2013.01); *G06K 9/6215* (2013.01); *G06K 9/6267* (2013.01); *G06T 7/0002* (2013.01); *G06T 7/0012* (2013.01); *A61B 6/466* (2013.01); *A61B 6/467* (2013.01); *A61B 6/469* (2013.01); *G06K 2009/4666* (2013.01); *G06T 2207/30004* (2013.01); *G06T 2207/30168* (2013.01)

(58) Field of Classification Search
CPC ................ A61B 6/5235; G06T 7/0002; G06T 2207/30168; G06T 2207/10016; G06T 2207/10072; G06T 2207/10132
See application file for complete search history.

(56) References Cited

FOREIGN PATENT DOCUMENTS

| | | |
|---|---|---|
| JP | 2002-222410 A | 8/2002 |
| JP | 2012-125297 A | 7/2012 |
| KR | 10-1307673 B1 | 9/2013 |

OTHER PUBLICATIONS

Machine Translation of First Office Action and Search issued in connection with corresponding CN Application No. 201580034306.1 dated Sep. 4, 2018.

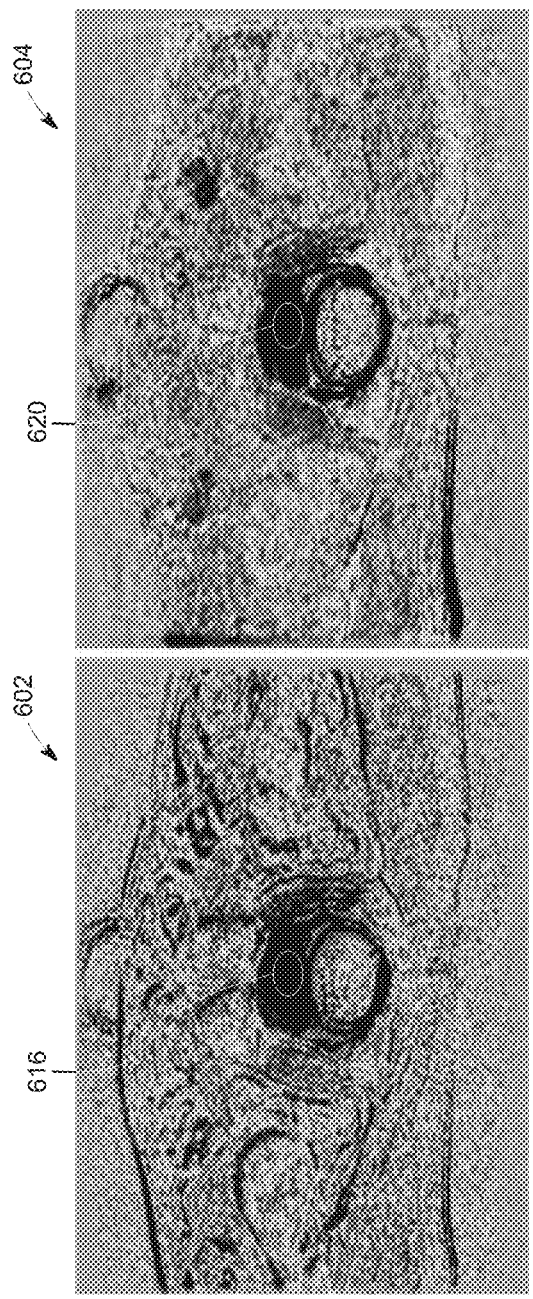

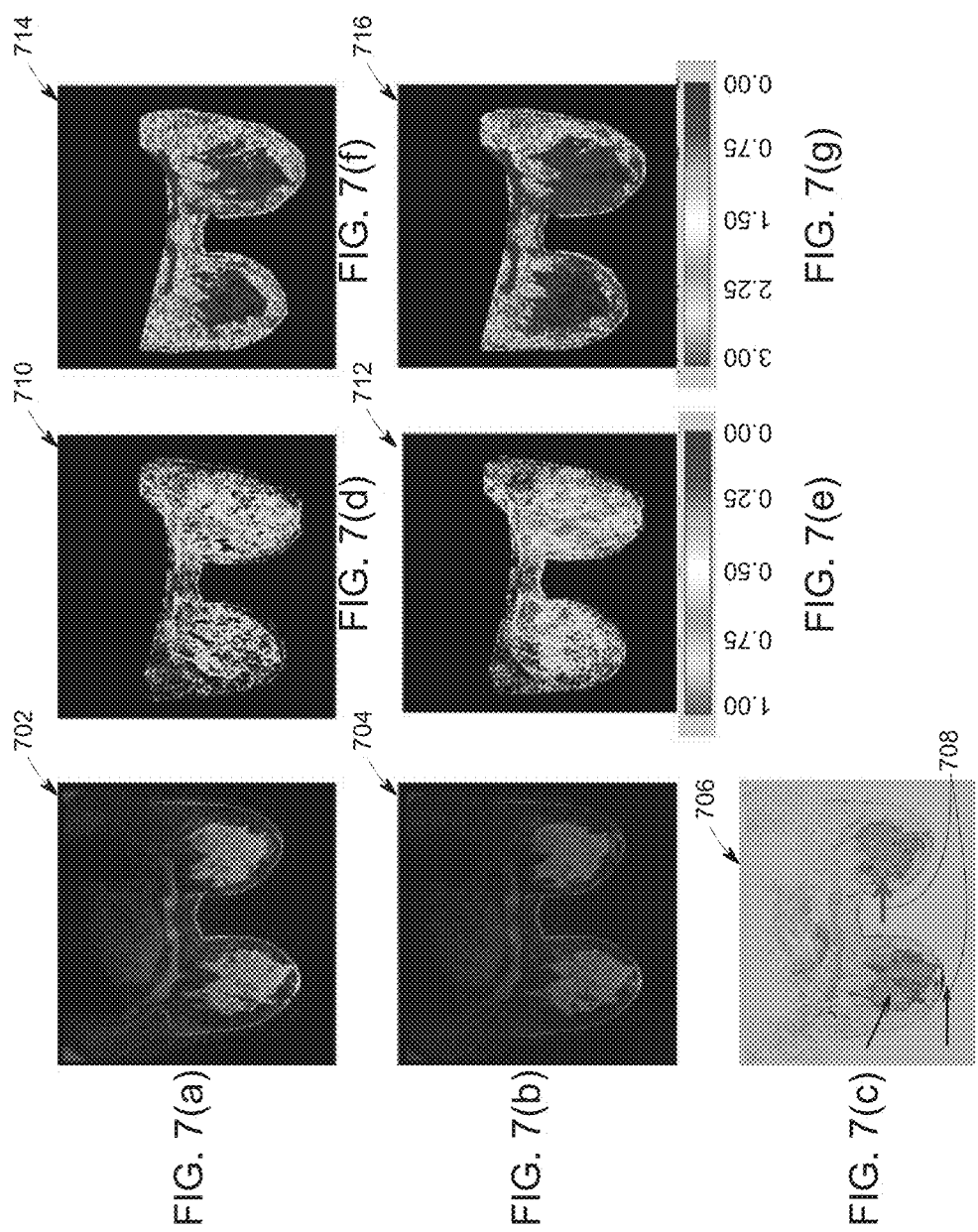

SYSTEM AND METHOD FOR EVALUATING MOTION CORRECTION IN DYNAMIC MEDICAL IMAGES

CROSS-REFERENCE TO RELATED APPLICATION

This national stage application under 35 U.S.C. § 371(c) of PCT Patent Application No. PCT/US2015/027432, filed on Apr. 24, 2015, which claims priority to India Patent Application No. 2108/CHE/2014, filed on Apr. 25, 2014, the disclosures of which are incorporated herein by reference in their entireties.

BACKGROUND

Embodiments of the present specification relate to imaging, and more particularly to evaluation of motion correction in dynamic medical images.

In modern healthcare facilities, non-invasive imaging systems are often used for identifying, diagnosing, and treating physical conditions. Medical imaging encompasses different non-invasive techniques used to image and visualize the internal structures and/or functional behavior (such as chemical or metabolic activity) of organs and tissues within a patient. Currently, a number of modalities of medical diagnostic and imaging systems exist, each typically operating on different physical principles to generate different types of images and information. These modalities include ultrasound systems, computed tomography (CT) systems, X-ray systems (including both conventional and digital or digitized imaging systems), positron emission tomography (PET) systems, single photon emission computed tomography (SPECT) systems, and magnetic resonance (MR) imaging systems.

In clinical practice, currently, two-dimensional (2D) medical images, three-dimensional (3D) medical images, and/or four-dimensional (4D) medical images are being routinely used for tracking contrast uptake, delivery of dose and to study time related variations of anatomy and physiology. Specifically, in Dynamic Contrast Enhanced magnetic resonance imaging (DCE-MRI), Dynamic Susceptibility Contrast MRI (DSC-MRI), or Dynamic Contrast Enhanced CT (DCE-CT), the uptake of contrast is analyzed for understanding the perfusion characteristics and cell structure, which may be indicative of tumor properties.

As will be appreciated, the dynamic 3D and/or 4D acquisitions typically entail long scan times for the complete scan. By way of example, acquiring data during 4D magnetic resonance imaging (MRI) generally calls for scan times that run into several minutes. The extended duration of the dynamic scan acquisition makes the data vulnerable to patient motion and related artifacts. Furthermore, during such long scans, patients under observation may experience voluntary and/or involuntary motion. Patient motion is one of the major challenges in the interpretation of image data. Particularly, patient motion hampers and/or distorts the quality of acquisition of image data. Some examples of patient motion during a scan may include a rapid shift, which may be caused due to the patient coughing or sneezing, motion due to breathing, and the like. Additionally, patient discomfort during the scan may also result in poor quality of data acquisition.

It may therefore be desirable to detect the presence of any patient motion during the acquisition of image data. The detection of motion may in turn be employed to aid in determining a corrective course of action. Early efforts for detecting patient motion during the scan procedure include use of feature-based methods. Other currently existing techniques entail use of registration methods for detecting and correcting patient motion. In addition, use of these techniques may entail user intervention or call for a trained clinician.

Furthermore, certain techniques for the acquisition of image data entail use of a contrast agent. By way of example, dynamic MRI with contrast (for example, DCE-MRI) is widely used for understanding the functional and metabolic aspects of disease (for example, tumor microvasculature, stroke, myocardial tissue infarction) and their progression. However, use of the contrast agent may adversely affect the detection of motion as uptake of the contrast agent may confound visual perception of motion. In addition, detection and correction of motion using the currently available techniques in the presence of contrast changes during the dynamic acquisition is a challenging task.

Motion correction is therefore regularly employed to correct the detected motion in the dynamic data. However, it is desirable to evaluate efficacy of the motion correction. Currently, the evaluation of the efficacy of motion correction is typically performed visually. Some techniques for the evaluation of motion correction entails comparing time-series data corresponding to a region of interest (ROI), while certain other techniques call for an assessment of the degree of dispersion of time-series data corresponding to a given ROI. Furthermore, one or more structures in the ROI may be observed to evaluate the motion correction. In addition, the motion correction may be evaluated via use of difference images. However, use of difference images is unsuitable for quantifying any improvement due to motion correction since contrast related signal changes can confound motion related changes. Therefore, the evaluation of motion correction using difference images is at best qualitative in nature and hinders comparison of motion correction efficacy across different sites or vendors.

BRIEF DESCRIPTION

In accordance with aspects of the present specification, a method for automated evaluation of motion correction is presented. The method includes identifying one or more regions of interest in each of a plurality of images corresponding to a subject of interest. Furthermore, the method includes selecting valid voxels in each of the one or more regions of interest in each of the plurality of images. The method also includes computing a similarity metric, a dispersion metric, or both the similarity metric and the dispersion metric for each region of interest in each of the plurality of images. Additionally, the method includes generating a similarity map, a dispersion map, or both the similarity map and the dispersion map based on the similarity metrics and the dispersion metrics corresponding to the one or more regions of interest.

In accordance with another aspect of the present specification, a system for automated evaluation of motion correction is presented. The system includes a motion correction evaluating platform configured to identify one or more regions of interest in each of a plurality of images corresponding to a subject of interest, select valid voxels in each of the one or more regions of interest in each of the plurality of images, compute a similarity metric, a dispersion metric, or both the similarity metric and the dispersion metric for each region of interest in each of the plurality of images, and generate a similarity map, a dispersion map, or both the similarity map and the dispersion map based on the similarity metrics and the dispersion metrics corresponding to the one or more regions of interest.

In accordance with yet another aspect of the present specification, an imaging system is presented. The system includes an acquisition subsystem configured to acquire image data corresponding to a subject of interest. Moreover, the system includes a processing subsystem in operative association with the acquisition subsystem and configured to process the acquired image data, wherein the processing subsystem comprises a motion correction evaluating platform configured to identify one or more regions of interest in each of a plurality of images corresponding to a subject of interest, select valid voxels in each of the one or more regions of interest in each of the plurality of images, compute a similarity metric, a dispersion metric, or both the similarity metric and the dispersion metric for each region of interest in each of the plurality of images, and generate a similarity map, a dispersion map, or both the similarity map and the dispersion map based on the similarity metrics and the dispersion metrics corresponding to the one or more regions of interest.

DRAWINGS

These and other features, aspects, and advantages of the present specification will become better understood when the following detailed description is read with reference to the accompanying drawings in which like characters represent like parts throughout the drawings, wherein.

Figure 1:
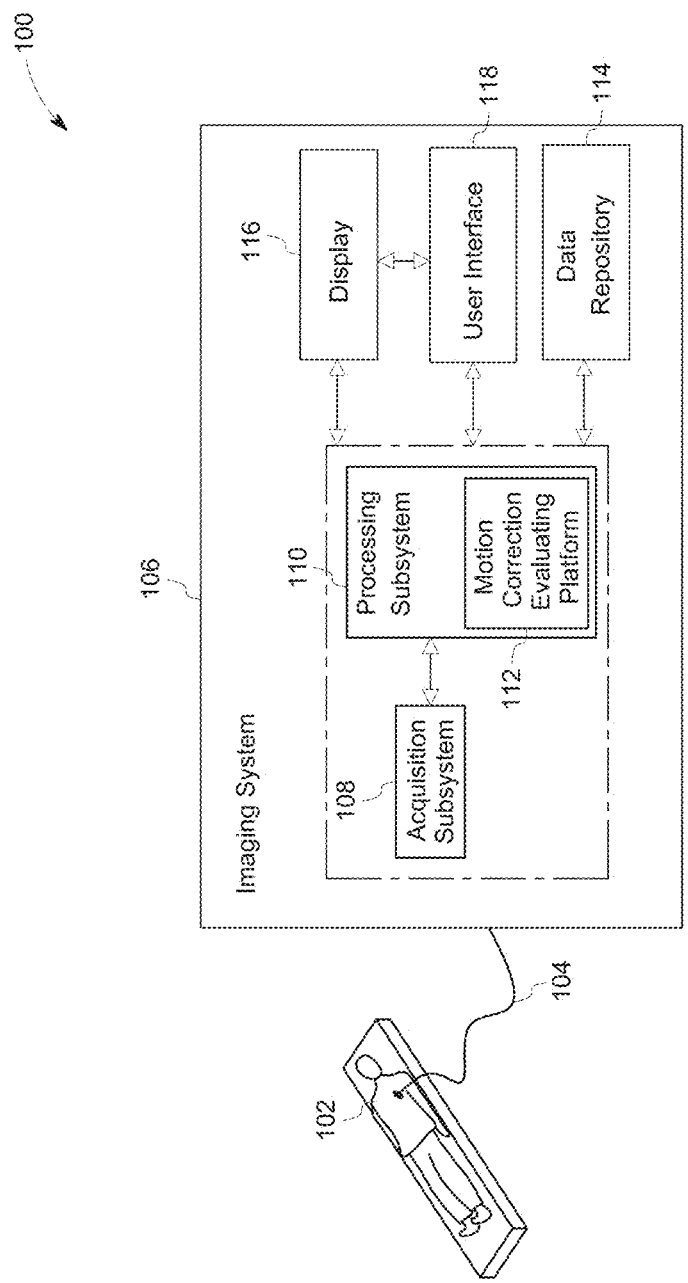
FIG. 1 is a diagrammatical illustration of a system for automated evaluation of efficacy of motion correction, in accordance with aspects of the present specification.
Figure 8:
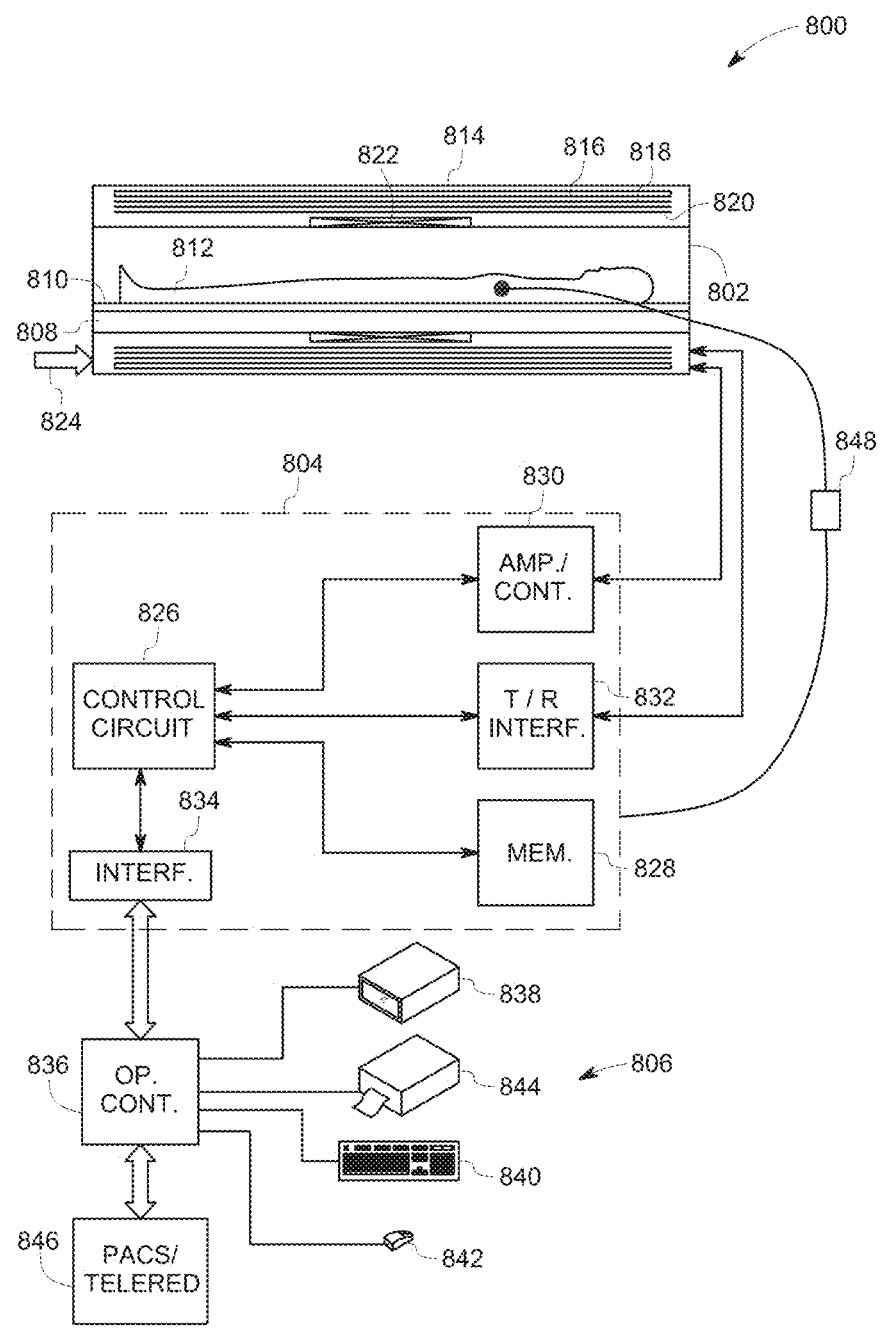

FIGS. 6(a)-6(h) and 7(a)-7(g) are diagrammatical representations of the exemplary method for automated evaluation of efficacy of motion correction, in accordance with aspects of the present specification; and FIG. 8 is a diagrammatical illustration of a magnetic resonance imaging system for use in the system of FIG. 1.

DETAILED DESCRIPTION

Medical images are routinely used for tracking contrast uptake, delivery of dose and to study time related variations of anatomy and physiology. However, the acquisition of these medical images typically entails long periods of time for the complete scan. Furthermore, patient motion during these long scans may hamper the quality of image data acquisition. Moreover, any motion experienced by a subject of interest such as a patient affects signal characteristics corresponding to an anatomical region in the patient being imaged. It is therefore desirable to detect any motion and suitably correct the detected motion to compensate for the patient motion. It may be noted that patient motion may include a rapid shift, a rotational motion, a lateral motion, an elastic motion, and the like.

Various motion correction techniques are typically employed to correct the dynamic data. Evaluation of efficacy of the motion correction is generally performed visually and/or via use of difference images. Use of visual methods and/or difference images is not suitable for quantifying the efficacy of the motion correction as contrast related signal changes can confound motion related changes.

Systems and methods for the automated evaluation and/or quantification of motion correction presented hereinafter enhance clinical workflow by robustly evaluating the efficacy of the motion correction. In addition, the systems and methods may also be employed to determine a further course of action for correcting the detected motion based on the evaluation of motion correction. More particularly, the systems and methods for the automated evaluation of motion correction described hereinafter provide a framework for robust appraisal and/or quantification of the corrected motion.

FIG. 1 is a block diagram of an exemplary system 100 for use in diagnostic imaging, in accordance with aspects of the present specification. The system 100 is configured to aid a clinician such as a radiologist in automatically assessing and quantifying the efficacy of motion correction, if any. More particularly, the system 100 may be configured to aid in enhancing clinical workflow by automatically quantifying the fidelity or efficacy of the motion correction. In addition, the system 100 may also be configured to facilitate determination of a suitable corrective course of action to further correct the detected motion or alter/adjust the acquisition of image data based on the evaluation of the motion correction.

In one embodiment, the system 100 may be configured to obtain image data corresponding to a subject of interest such as a patient 102. In one embodiment, an image acquisition device 104 may be employed to acquire image data. However, other embodiments of the system 100 may obviate the need for use of the image acquisition device 104. The image acquisition device 104 may include a probe, where the probe may include an invasive probe, or a non-invasive or external probe that is configured to aid in the acquisition of the image data. In certain other embodiments, image data may be acquired via one or more sensors (not shown) that may be disposed on the patient 102. By way of example, the sensors may include physiological sensors (not shown) such as electrocardiogram (ECG) sensors and/or positional sensors such as electromagnetic field sensors or inertial sensors. These sensors may be operationally coupled to a data acquisition device, such as an imaging system, via leads (not shown), for example. Use of one or more detectors or detector arrays for acquiring image data is also envisaged.

It may be noted that the image data obtained by the system 100 may include original image data corresponding to an anatomical region in the patient 102 being imaged that is acquired over a determined period of time. Furthermore, the image data may also include motion corrected image data. In particular, the motion corrected image data may correspond to the original image data that has been processed to correct any detected motion.

The system 100 may also include a medical imaging system 106. In one embodiment, the medical imaging system 106 may be in operative association with the image acquisition device 104. In addition, in the present example, the medical imaging system 106 may be a magnetic resonance imaging (MRI) system. It should be noted that although the exemplary embodiments illustrated hereinafter are described in the context of a medical imaging system, other imaging systems and applications such as industrial imaging systems and non-destructive evaluation and inspection systems, such as pipeline inspection systems, liquid reactor inspection systems, are also contemplated. Additionally, the exemplary embodiments illustrated and described hereinafter may find application in multi-modality imaging systems that employ magnetic resonance (MR) imaging in conjunction with other imaging modalities, position-tracking systems or other sensor systems. For example, the multi-modality imaging system may include a positron emission tomography (PET) imaging system-MRI system.

Furthermore, it should be noted that although the exemplary embodiments illustrated hereinafter are described in the context of a medical imaging system, such as the MRI system, use of other imaging systems, such as, but not limited to, a computed tomography (CT) imaging system, a contrast enhanced ultrasound imaging system, an X-ray imaging system, an optical imaging system, a positron emission tomography (PET) imaging system, an ultrasound imaging system, a contrast enhanced X-ray imaging system, and other imaging systems is also contemplated in accordance with aspects of the present specification.

As noted hereinabove, in a presently contemplated configuration, the medical imaging system 106 is an MRI system. The medical imaging system 106 may include an acquisition subsystem 108 and a processing subsystem 110, in one embodiment. Further, the acquisition subsystem 108 of the medical imaging system 106 may be configured to acquire image data representative of one or more anatomical regions in the patient 102 via the image acquisition device 104, in one embodiment. However, in certain other embodiments, the acquisition subsystem 108 may be configured to acquire image data without the use of the image acquisition device 104. Moreover, as noted hereinabove, the image data acquired by the medical imaging system 106 and the acquisition subsystem 108 in particular includes original image data and the corresponding motion corrected image data.

The system 100 and more particularly the acquisition subsystem 108 may be configured to acquire image data corresponding to an anatomical region in the patient 102 in real-time. Alternatively, the images may be obtained by the acquisition subsystem 108 from an archival site, a database, or an optical data storage article. For example, the acquisition subsystem 108 may be configured to acquire images stored in the optical data storage article. It may be noted that the optical data storage article may be an optical storage medium, such as a compact disc (CD), a digital versatile disc (DVD), multi-layer structures, such as DVD-5 or DVD-9, multi-sided structures, such as DVD-10 or DVD-18, a high definition digital versatile disc (HD-DVD), a Blu-ray disc, a near field optical storage disc, a holographic storage medium, or another like volumetric optical storage medium, such as, for example, two-photon or multi-photon absorption storage format.

In one example, the anatomical region being imaged may include any tissue that can be perfused. Additionally, the anatomical region may include any tissue that has a potential for perfusion deficit. Some non-limiting examples of the anatomical regions of interest include the breasts, the prostrate, bones, the kidneys, the lungs, or the uterus in the patient 102.

The acquired image data may include a plurality of images. By way of example, the acquired image data may include a plurality of two-dimensional (2D) images acquired over time, where the plurality of 2D images corresponds to the anatomical region being imaged. The acquired image data may also include three-dimensional (3D) images corresponding to the anatomical region acquired over a determined period of time. It may be noted that the 3D images corresponding to the anatomical region acquired over a period of time may be representative of four-dimensional (4D) images corresponding to the anatomical region. It may also be noted that although the present specification is described in terms of 4D images, use of the present specification with images having higher or lower dimensions is also envisaged. It may be noted that the terms plurality of images and time-series image data may be used interchangeably.

Moreover, in one embodiment, the acquired image data may be representative of dynamic data. In particular, the acquired image data may include contrast enhanced dynamic data. Accordingly, the acquisition of image data may entail acquiring one or more images accompanied with the use of a contrast agent. The contrast agent may include an endogenous contrast agent or an exogenous contrast agent.

It may be noted that in certain situations an exogenous contrast agent may be used. In such situations, one or more images of the time-series image data corresponding to the anatomical region being imaged may be acquired prior to administering the exogenous contrast agent to the patient 102. The exogenous contrast agent may subsequently be administered to the patient 102. In one example, the contrast agent may include a gadolinium based contrast agent. One or more images may be acquired subsequent to the exogenous contrast agent being administered to the patient 102.

Furthermore, in situations where the endogenous contrast agent is utilized, the anatomical region or a marker such as blood may be "prepared" for contrast. In one example, the marker such as blood may be prepared for contrast using magnetization. More particularly, blood may be magnetically labeled and the loss of magnetization may be tracked over time. In another example, the anatomical region may be prepared for contrast via use of a genetic marker. In this example, the anatomical region may be configured to provide contrast in response to a stimulus such as light.

Also, it may be noted that the dynamic data may include dynamic contrast enhanced images such as dynamic contrast enhanced (DCE) magnetic resonance images, dynamic susceptibility contrast (DSC) magnetic resonance images, arterial spin labeled (ASL) images, contrast enhanced X-ray images, contrast enhanced computed tomography (CT) images, contrast enhanced ultrasound images, or combinations thereof.

Additionally, the acquired image data may be processed by the processing subsystem 110, where the processing subsystem 110 is operatively coupled to the acquisition subsystem 108. According to aspects of the present specification, the image data acquired and/or processed by the medical imaging system 106 may be employed to aid a clinician by automatically evaluating and/or quantifying the efficacy of motion correction using the acquired time-series image data.

In certain embodiments, the processing subsystem 110 may be further coupled to a storage system, such as the data repository 114, where the data repository 114 may be configured to store the acquired and/or processed image data. Furthermore, the image data acquired by the acquisition subsystem 108 may be stored in the data repository 114 (see FIG. 1). In certain embodiments, the data repository 114 may include a local database.

Additionally, in accordance with exemplary aspects of the present specification, the processing subsystem 110 may include a motion correction evaluating platform 112 that is configured to aid in the automated evaluation of the efficacy of motion correction of the dynamic image data corresponding to the patient 102, if any, during the imaging procedure. More particularly, the motion correction evaluating platform 112 may be configured to automatically evaluate and/or quantify the efficacy of the motion correction using the acquired time-series image data. The motion correction evaluating platform 112 may also be referred to as an evaluating platform.

The evaluating platform 112 may be configured to "evaluate" and/or quantify the efficacy or fidelity of the motion correction of the acquired time-series image data. As previously noted, the acquired images include original image data and the corresponding motion corrected image data. In accordance with aspects of the present specification, the evaluating platform 112 may be configured to process the original image data and the corresponding motion corrected image data to assess the fidelity of the motion correction. To that end, the evaluating platform 112 may be configured to compute a similarity metric and/or a dispersion metric corresponding to the original image data and the corresponding motion corrected image data. In particular, the evaluating platform 112 may be configured to compute the similarity metric and the dispersion metric corresponding to valid voxels in the image data being processed. The evaluating platform 112 may also be configured to generate a similarity map and/or a dispersion map based on the computed metrics. These maps may be visualized on a display to aid the clinician in determining the efficacy of the motion correction. Alternatively, indicators that are representative of the efficacy of motion correction may be generated by the evaluating platform 112 and displayed on or about the images and/or metric maps. The functioning of the evaluating platform 112 will be described in greater detail with reference to FIGS. 2-7.

In addition, as illustrated in FIG. 1, the medical imaging system 106 may include a display 116 and a user interface 118. In certain embodiments, such as in a touch screen, the display 116 and the user interface 118 may overlap. Also, in some embodiments, the display 116 and the user interface 118 may include a common area. In accordance with aspects of the present specification, the display 116 of the medical imaging system 106 may be configured to display one or more images corresponding to the anatomical region, indicator(s) representative of the evaluation of the efficacy of motion correction generated by the evaluating platform 112 in the medical imaging system 106, the corrected images, and the like.

Also, the user interface 118 of the medical imaging system 106 may include a human interface device (not shown) configured to aid the clinician in manipulating image data displayed on the display 116. The human interface device may include a mouse-type device, a trackball, a joystick, a stylus, or a touch screen configured to facilitate the clinician to identify the one or more regions of interest. However, as will be appreciated, other human interface devices, such as, but not limited to, a touch screen, may also be employed. Furthermore, in accordance with aspects of the present specification, the user interface 118 may be configured to aid the clinician in navigating through the images received by the medical imaging system 106. Additionally, the user interface 118 may also be configured to aid in manipulating and/or organizing the images displayed on the display 116. The automated method of evaluating and/or quantifying the motion correction using the acquired time-series image data will be described in greater detail with reference to FIGS. 2-7.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the invention. Thus, those skilled in the art will appreciate that the present system 100 is provided by way of example, and the present specification is in no way limited by the specific system configuration.

Figure 2:
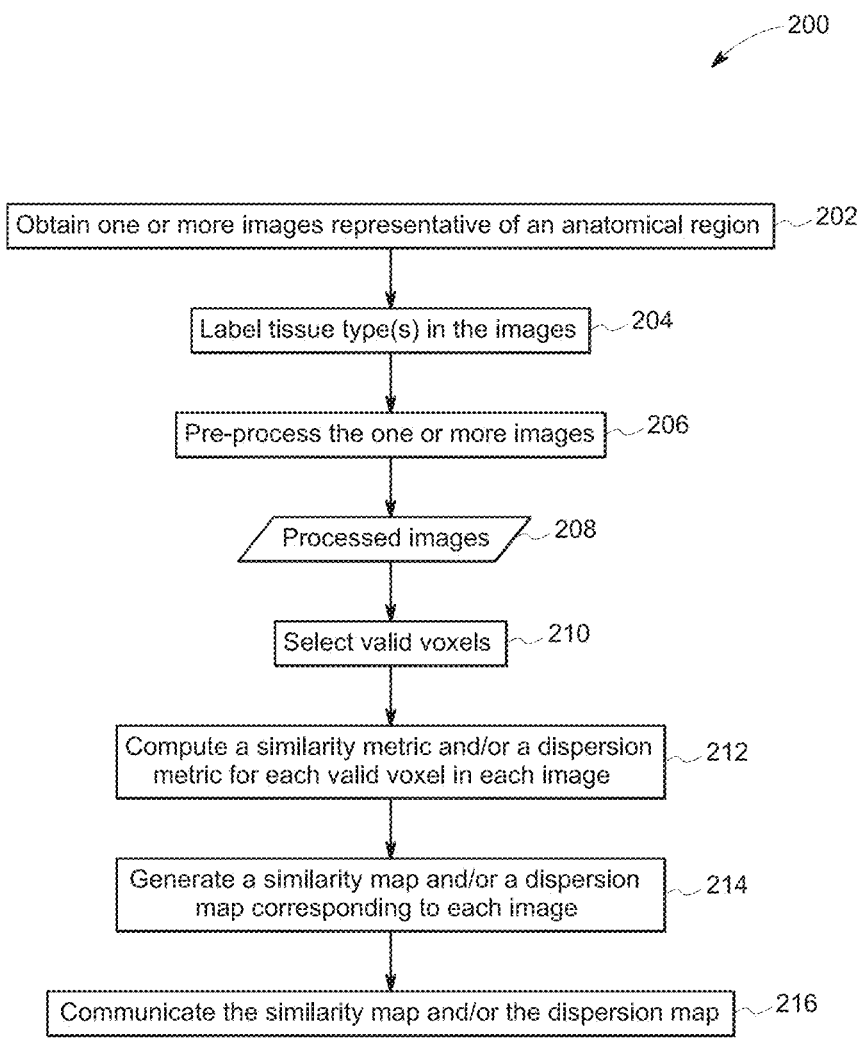
FIG. 2 is a flow chart depicting an exemplary method for automated evaluation of efficacy of motion correction, in accordance with aspects of the present specification.

Turning now to FIG. 2, a flow chart of exemplary logic 200 for a method for automatically evaluating motion correction using DCE MRI images, for example, is depicted. As previously noted, these DCE MRI images may correspond to an anatomical region in a patient such as the patient 102 of FIG. 1. Any patient motion may affect signal characteristics corresponding to the anatomical region being imaged. The method of FIG. 2 is described in terms of the various components of FIG. 1.

The method 200 may be described in a general context of computer executable instructions. Generally, computer executable instructions may include routines, programs, objects, components, data structures, procedures, modules, functions, and the like that perform particular functions or implement particular abstract data types. In certain embodiments, the computer executable instructions may be located in computer storage media, such as a memory, local to an imaging system 106 (see FIG. 1) and in operative association with a processing subsystem. In certain other embodiments, the computer executable instructions may be located in computer storage media, such as memory storage devices, that are removed from the imaging system. Moreover, the method for the automated evaluation of motion correction includes a sequence of operations that may be implemented in hardware, software, or combinations thereof.

As will be appreciated during a typical scan session, a subject such as the patient 102 is positioned for imaging and the clinician attempts to image a desired anatomical region in the patient. Accordingly, the patient may be positioned for imaging. Following any pre-imaging procedures, an anatomical region for imaging may be selected. In one example, the clinician may identify the anatomical region in the patient to be imaged. As previously noted, the anatomical region may include any tissue that can be perfused or a tissue that has a potential for perfusion deficit. Some non-limiting examples of the anatomical regions include the head, breasts, the prostrate, bones, the kidneys, cardiac regions, the lungs, the liver, the cervix, or the uterus in the patient. In certain other embodiments, the system 100 may be configured to automatically select the anatomical region to be imaged based on the position of the patient in/on the imaging system, for example.

Subsequent to the selection of the anatomical region, image data corresponding to the selected anatomical region in the patient may be obtained, as depicted by step 202. In one embodiment, the image data may be obtained in real-time. However, in certain other embodiments, previously acquired data may be retrieved from a data repository, such as the data repository 114. As previously noted, any motion experienced by the patient during the scanning procedure may adversely affect the quality of acquired image data corresponding to the anatomical region being imaged. In particular, patient motion, if any, may alter the signal characteristics corresponding to the anatomical region being imaged. Moreover, use of the contrast agent may also adversely affect the detection of motion as uptake of the contrast agent may confound visual perception of motion.

Accordingly, in one embodiment, the signal characteristics corresponding to the anatomical region being imaged may be monitored and evaluated to detect any patient motion. Furthermore, the detected motion in the signal characteristics may be corrected thereby generating motion corrected image data. Hence, the image data obtained at step 202 may include original time-series motion corrupted image or signal data and corresponding motion corrected image or signal data.

Moreover, the time-series image data obtained at step 202 may include dynamic 2D images, dynamic 3D images, and/or 4D images. In particular, these dynamic images include 2D and/or 3D images acquired over a determined period of time. Further, the determined period of time may include the scan time, for example.

It may be noted that in the example of FIG. 2, the method is described with reference to the DCE MRI 4D images corresponding to the anatomical region being imaged. Although the method of FIG. 2 is described in terms of automatically evaluating the efficacy of motion correction using DCE MRI images, use of this method for automatically evaluating the efficacy of motion correction using other images that include dynamic data is also envisaged. In addition, the method for automatically evaluating the efficacy of motion correction may also be performed using other images such as, but not limited to, DSC images, arterial spin labeling (ASL) images, contrast enhanced X-ray images, contrast enhanced CT images, contrast enhanced ultrasound images, or combinations thereof.

As previously noted, the acquired image data may include contrast enhanced dynamic data. Accordingly, the acquisition of image data may entail the use of a contrast agent, where the contrast agent may be an endogenous contrast agent or an exogenous contrast agent. In situations that call for the use of the exogenous contrast agent, one or more images may be acquired prior to administering the exogenous contrast agent to the patient. Subsequently, the exogenous contrast agent may be administered to the patient. One or more images may then be acquired ensuing the administering of the exogenous contrast agent. However, in situations where the endogenous contrast agent is used, the anatomical region may be prepared for contrast.

The acquisition of the images, especially 4D DCE MRI images, necessitates long scan times. Patients undergoing these long scans may experience voluntary and/or involuntary motion. The motion of the patient may adversely affect the quality of the acquired image data. Additionally, use of the contrast agent may adversely affect the detection of motion as the uptake of the contrast agent may confound visual perception of motion. Accordingly, the acquired original image data is typically processed to detect and correct the detected motion thereby supporting any remedial action to correct the detected motion. Furthermore, once the dynamic image data has been corrected for motion, it is desirable to evaluate and/or quantify the "efficacy" or "fidelity" of the motion correction.

As will be appreciated, the anatomical region being imaged may include one or more tissue types. It may be assumed that the tissue type is homogeneous for a given region of interest (ROI) within the anatomical region being imaged. Accordingly, the anatomical region being imaged may be divided into one or more regions of interest (ROIs) based on a corresponding tissue type. It may be noted that in one embodiment, regions of interest may be automatically identified by the system. Alternatively, in certain embodiments, the regions of interest may be manually prescribed by the clinician.

Accordingly, at step 204, the one or more regions of interest may be identified. In certain embodiments, the one or more regions may be identified based on a tissue type. In addition, the one or more regions may be labeled to identify the corresponding tissue type. By way of example, if the head is being imaged, the different tissue types may include the white matter, the grey matter and the cerebro-spinal fluid (CSF). Also, if the prostate is being imaged, the different tissue types may include the central zone and the peripheral zone. The different tissue types may be suitably labeled. In one example, the tissue types may be labeled via use of a shape indicator. The shape indicators may include a square shape, a circular shape, a rectangular shape, a triangular shape, and the like. Alternatively, the labels may include text and/or numerals. In certain other embodiments, the labels may include a combination of shape indicators, text, and numerals. It may be noted that in certain embodiments, the one or more regions of interest may be identified by a user such as the clinician. Alternatively, in certain other embodiments, the one or more regions may be automatically identified by the system 100 based on the tissue type.

Once the tissue types have been labeled, the images may be processed to remove any noise or spurious transients, as indicated by step 206. In one example, signal data corresponding to the images may be normalized to remove any noise signals in the images. Alternatively, the images may be processed via use of filters to remove any noise. The acquired images that have been labeled and/or filtered may generally be referred to as processed images 208.

As previously noted, currently available techniques used for evaluating the efficacy of motion correction entail visual inspection of the motion corrected images, comparing time-series data in a ROI and assessing the degree of dispersion of time-series data in the given ROI, observing certain structures, or using difference images. Use of difference images is not suitable for quantifying improvement in motion correction since contrast related signal changes can confound motion related changes. Therefore, the evaluation of motion correction using difference images is at best qualitative in nature.

The shortcomings of the currently available techniques may be circumvented via use of quantitative metrics to assess the fidelity of motion correction with dynamic time-series image data. In accordance with aspects of the present specification, one or more time-series image data derived metrics corresponding to the processed images may be computed to aid in evaluating and/or quantifying the efficacy of the motion correction.

In preparation for the computation of the time-series image data derived metrics, the time-series image data obtained at step 202 may be normalized, in one embodiment. To that end, signal characteristics $S_t$ corresponding to each element in images 208 may be obtained. More particularly, the signal characteristics corresponding to each element in the images may be determined, thereby obtaining 3D time-series signal data. In one embodiment, the signal characteristics may include a magnetic resonance (MR) signal that has been modulated by contrast flow. The elements in the images 208 may correspond to pixels or voxels in the images. Also, the determined period of time may correspond to the scan time.

The 3D times-series signal data $S_t$ may also be normalized for identifying noise and/or spurious transients. In one embodiment, the signal data $S_t$ may be normalized based on equation (1).

$$S_{norm} = (S_t - S_0)/S_0 \qquad (1)$$

where $S_0$ is representative of a signal at a first time point $t_0$.

It may be noted that in certain embodiments, the time-series image data may be normalized using a baseline signal. However, in certain other embodiments, the time-series image data may be converted into quantitative values. By way of example, the quantitative values may be representative of a concentration of injected contrast agent that is computed using a mapping function between signal intensity and contrast agent properties such as the relaxivity of gadolinium. The quantitative values may be then thresholded to remove any spurious time-series data.

The normalized signal data $S_{tnorm}$ may include "rogue" voxels and/or spurious transients that corrupt the computation of the metrics. It may be noted that the rogue voxels may also be referred to as "noise" voxels. Hence, it may be desirable to remove the noise voxels prior to the computation of the metrics. Accordingly, at step 210, "valid" voxels may be selected, while the rogue or noise voxels are removed from the normalized signal data $S_{tnorm}$. Furthermore, a peak time-point $t_p$ may be computed for a given time-series data. The peak time point $t_p$ is representative of a time-point at which the normalized signal intensity has a maximum value. In addition, the normalized signal intensity at the peak time point $t_p$ may be used in the identification of the rogue voxels. In one embodiment, a determined threshold may be used to identify the valid voxels. In certain embodiments, the determined threshold may be a "fixed" threshold, while in certain other embodiments, the determined threshold may be an adaptive threshold. One example the determined threshold is presented in equation (2).

$$\text{Max}(S_{tnorm}) > 0 \text{ and } \min(S_{tnorm}(t > t_p)) > 2.5\% \quad (2)$$

In accordance with aspects of the present specification, any voxel that satisfies the criteria of equation (2) may be recognized as a valid voxel. Additionally, any voxel that fails to satisfy the criteria of equation (2) may be identified as a "rogue" voxel or a transient. Also, the rogue voxels may be assigned a value of zero for use in any further processing of the image data.

In accordance with further aspects of the present specification, once the valid voxels are identified, time-series based quantitative metrics corresponding to the anatomical region may be determined, as depicted by step 212. The quantitative metrics may include a similarity metric and/or a dispersion metric. The similarity metric may include a correlation metric, in one embodiment. Also, the dispersion metric may include a variance, a Z-score, and the like. Furthermore, these quantitative metrics may be determined using the time-series image data.

In certain embodiments, the similarity metric and/or the dispersion metric corresponding to each region of interest in the anatomical region identified at step 204 may be computed. Accordingly, at step 212, for each region of interest, a time-series derived similarity metric such as a local correlation metric (LCM) may be computed. As previously noted, the ROI may be provided as user input. Alternatively, the ROI may be automatically generated as an output of the tissue classification or labeling of step 204. In particular, a similarity metric for each valid voxel in the ROI may be computed. The similarity metric is representative of a similarity among the valid voxels in the given ROI and a determined neighborhood in that ROI. Alternatively, a similarity metric between a given valid voxel time-series data and its neighboring voxel time-series data in a given ROI may be computed. By way of example, the time-series image data may include dynamic images $I_1, I_2, I_3, \ldots, I_m$. Furthermore, each dynamic image $I_m$ may include n ROIs such as $ROI_1, ROI_2, \ldots ROI_n$. Moreover, each ROI may in turn include l valid voxels such as $v_1, v_2, \ldots v_l$. Accordingly, for a given ROI, a similarity metric is computed among all the valid voxel time-series data in a determined $ROI_n$. Alternatively, in a given $ROI_n$, a central voxel may be identified. Furthermore, a similarity metric between the time-series data corresponding to the central voxel and the time-series data corresponding to the neighboring voxels may be computed. The computation of the LCM corresponding to the regions of interest will be described in greater detail with reference to FIG. 3.

Furthermore, motion experienced by the patient and contrast uptake in the anatomical region result in changes in the signal characteristics or data corresponding to the anatomical region being imaged. Hence, use of just a simple time-series distance metric is insufficient for identifying changes in the signal characteristics due to patient motion. Moreover, it has also been observed that at each time point, variance in signal characteristics is reduced post motion correction.

In accordance with aspects of the present specification, a local dispersion metric (LDM) may be used in conjunction with the LCM to enhance the evaluation of the efficacy of motion correction, thereby providing a quantitative evaluation of the efficacy of motion correction in the dynamic MRI images. It may be noted that while the LCM primarily reflects temporal continuity in a given ROI, the LDM captures the spatial continuity in the given ROI. Hence, the LCM and the LDM are complementary to one another.

To that end, at step 212, in addition to the similarity metric, a dispersion metric corresponding to each valid voxel in a given ROI may also be computed. In one embodiment, for each ROI, a time-series derived dispersion metric such as a LDM may be computed. More particularly, for each valid voxel in the given ROI, a dispersion metric that is representative of a dispersion of the signal characteristics between a given valid voxel and corresponding valid voxels in the neighborhood region around the valid voxel may be computed at a given point in time. By way of example, the time-series image data may include dynamic images $I_1, I_2, I_3, \ldots, I_m$, where each dynamic image $I_m$ may include n ROIs such as $ROI_1, ROI_2, \ldots, ROI_n$. Also, each ROI may in turn include l valid voxels such as $v_1, v_2, \ldots v_l$. Accordingly, for a given valid voxel $v_l$ in a determined $ROI_n$, a dispersion metric that is representative of the variance or dispersion of the signal characteristics corresponding to the given valid voxel $v_l$ and the signal characteristics corresponding to valid voxels in neighborhood of the given valid voxel $v_l$ may be computed at each time point. Once the dispersion metrics corresponding to each valid voxel in each ROI is computed, the LDM may be computed using the computed dispersion metrics. The computation of the LDM corresponding to the regions of interest will be described in greater detail with reference to FIGS. 4-5.

With continuing reference to FIG. 2, once the LCMs and LDMs corresponding to each ROI in the times-series image data are computed, a similarity map and/or a dispersion map may be generated, as indicated by step 214. In particular, the LCMs may be used to generate a similarity map, while the LDMs may be employed to generate a dispersion map. These maps may be used in synchrony to evaluate the efficacy of motion correction in the dynamic images.

As previously noted, while the LCM primarily reflects temporal continuity in a given ROI, the LDM captures the spatial continuity in the given ROI, thereby rendering the LCM and LDM maps complementary. Accordingly, the LCM and LDM maps may be used in tandem as a standardized mechanism for reporting any improvement in dynamic data after motion correction. These maps provide a quantitative representation of the similarity and/or dispersion between the original motion corrupted image data and the corresponding motion corrected image data. In certain embodiments, the maps may be color coded, where different colors are representative of different values of similarity or dispersion of the time-series image data. Alternatively, shaped indicators, text, numerals, or combinations thereof may be used to embody the different values of similarity or dispersion of the time-series image data.

Use of these maps allows easy comparison of performance of different algorithms on the acquired image data. Moreover, as previously noted, signal characteristics or signal intensity data have been employed for the computation of the metrics such as LCM and LDM. Also, the signal data can be corrupted by signal inhomogeneity related artifacts, Use of normalized and filtered data enhances the estimation of the similarity metric (LCM) and/or the dispersion metric (LDM) even in the presence of the signal inhomogeneity related artifacts.

Subsequently, at step 216, the similarity map and/or the dispersion map may be communicated to a clinician to aid in evaluating the fidelity of the motion correction. In certain embodiments, these maps may be visualized on a display, such as the display 116 of FIG. 1.

Additionally, at step 216, one or more of the original image data, the motion corrected data, the signal characteristics, the detected motion, the indicators of the evaluation of the efficacy of motion correction, and the like may be communicated to the clinician. It may be noted that in certain embodiments, step 216 may be an optional step. In one embodiment, one or more of the original image data, the similarity map, the dispersion map, the detected motion, and/or the corrected image may be communicated to the clinician by visualization on a display, such as the display 116 of FIG. 1. This visual display may aid the clinician in the enhanced evaluation of the efficacy of the motion correction. Alternatively, information related to one or more of the original image data, the similarity map, the dispersion map, the detected motion, and/or the corrected image may be communicated to the clinician via other means such as an audio signal.

As noted with reference to FIG. 2, the time-series quantitative metrics such as the LCM and/or the LDM corresponding to each ROI in the anatomical region being imaged are computed. However, in other embodiments, signal characteristics corresponding to the entire anatomical region may be processed to generate the metrics and/or the maps.

Figure 3:
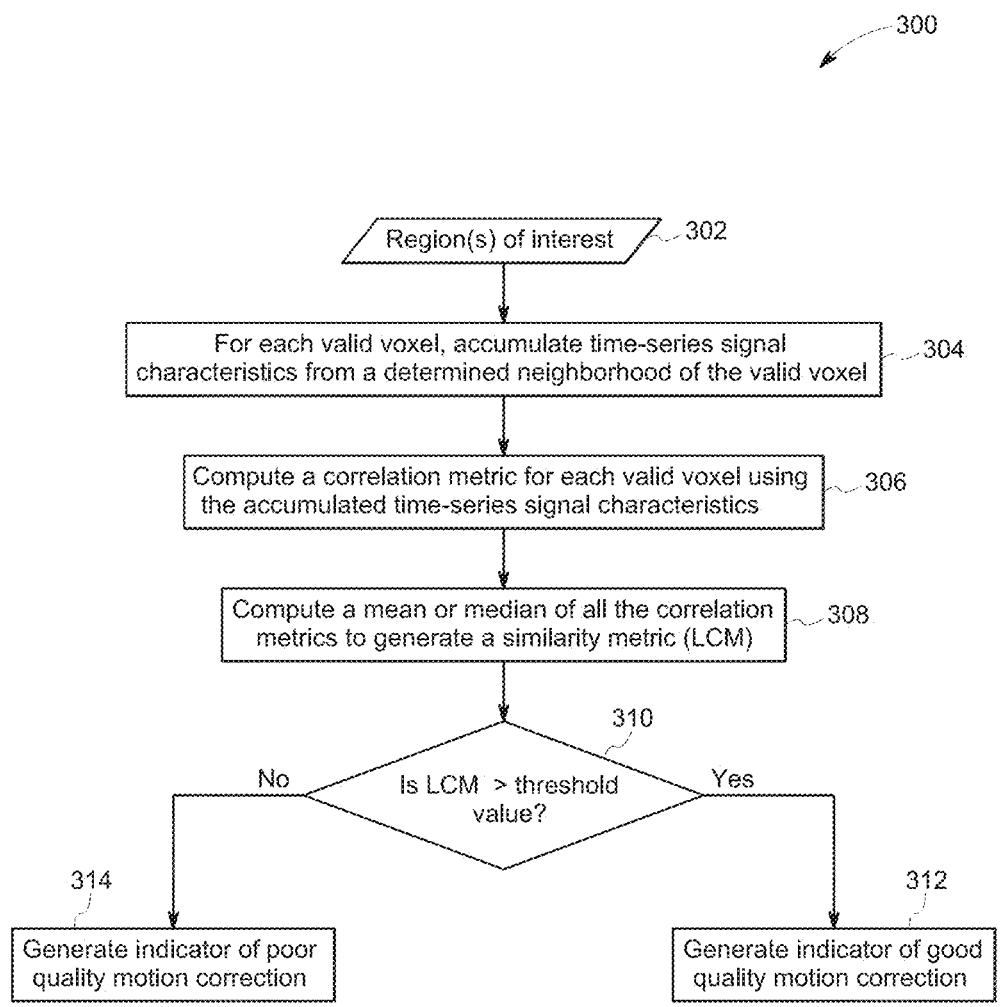
FIG. 3 is a flow chart depicting an exemplary method for determining a local similarity or correlation metric, in accordance with aspects of the present specification.

Referring now to FIG. 3, a flowchart 300 depicting a method of computing a similarity metric such as the LCM using acquired image data is presented. In particular, FIG. 3 depicts the computation of the LCM of step 212 of FIG. 2. The method of FIG. 3 is described in terms of the various components of FIGS. 1-2. As noted with reference to FIG. 2, each image is divided into one or more regions of interest based on the corresponding tissue type. Accordingly, in the method of FIG. 3, regions of interest 302 corresponding to the processed images 208 may be obtained. Each of the regions of interest in 302 may be identified based on a corresponding label. In one embodiment, a mask may be employed to delineate each ROI 302 in the processed images. Furthermore, it may be noted that each ROI 302 in the processed image includes one or more valid voxels, while the rogue or noise voxels have been removed.

Moreover, at step 304, signal characteristics or signal intensity data corresponding to each valid voxel in a given ROI 302 across time may be obtained. In particular, for each valid voxel, time-series signal curves or characteristics that correspond to valid voxels from a determined neighborhood may be accumulated. In one example, the determined neighborhood may include a 3×3×3 neighborhood that surrounds a given valid voxel. By way of example, for a valid voxel $v_j$, signal characteristics corresponding to valid voxels in the determined neighborhood in each of the time-series processed images may be obtained. Accordingly, three-dimensional (3D) time-series signal data may be acquired. In one embodiment, the signal characteristics may include a magnetic resonance (MR) signal that has been modulated by contrast flow.

Subsequently, at step 306, a similarity metric corresponding to the given valid voxel in the ROI 302 may be computed. More particularly, the similarity metric corresponding to the given valid voxel may be computed using the accumulated time-series signal curves that correspond to the valid voxels in the determined neighborhood. In one embodiment, the similarity metric may include a correlation coefficient. Once the correlation coefficient corresponding to each valid voxel in the given region of interest is computed, a mean of all the computed correlation coefficients may be determined, as depicted by step 308. This computed mean of all the correlation coefficients may be representative of the similarity metric. In certain other embodiments, other statistical measures such as a median of all the correlation coefficients may be used as the similarity metric. The similarity metric so determined may be referred to as a local correlation metric (LCM).

In accordance with aspects of the present specification, a higher value of the LCM is representative of better alignment of the signal data in the given ROI at different time points. Accordingly, it may be desirable to quantify the LCM. In one embodiment, the LCM determined at step 308 may be compared with a threshold value to quantify the LCM, as indicated by step 310. It may be noted that each region of interest 302 may be assigned a corresponding threshold value based on the tissue type of that region of interest. The threshold value may be externally supplied, in certain embodiments. However, in certain other embodiments, the threshold value may be automatically assigned by the system 100, for example.

At step 310, if it is verified that the value of the LCM is greater than the corresponding threshold value, then it may be deduced that the LCM has a high value, where the high value of the LCM is generally indicative of better alignment of the signal data post motion correction. Accordingly, at step 312, an indicator of the "good" alignment of the signal data post motion correction may be generated. However, at step 310, if it is verified that the value of the LCM is lower than the corresponding threshold value, then it may be inferred that the LCM has a lower value, where the lower LCM value is generally indicative of poor alignment of the signal data post motion correction. The indicator may be visualized on the image and/or a similarity map. Additionally, at step 314, an indicator of the "poor" alignment of the signal data post motion correction may be generated and visualized on the image or a similarity map. This process of computing the LCM may be repeated for each ROI in the anatomical region being imaged.

As noted hereinabove, motion experienced by the patient and contrast uptake in the anatomical region result in changes in signal data or characteristics corresponding to the anatomical region being imaged. Hence, use of just a simple time-series distance metric is insufficient for identifying changes in the signal data due to patient motion. In accordance with aspects of the present specification, a local dispersion metric (LDM) may be used in conjunction with the LCM to enhance the evaluation of the efficacy of motion correction, thereby providing a quantitative evaluation of the efficacy of motion correction in the dynamic MRI images.

Figure 4:
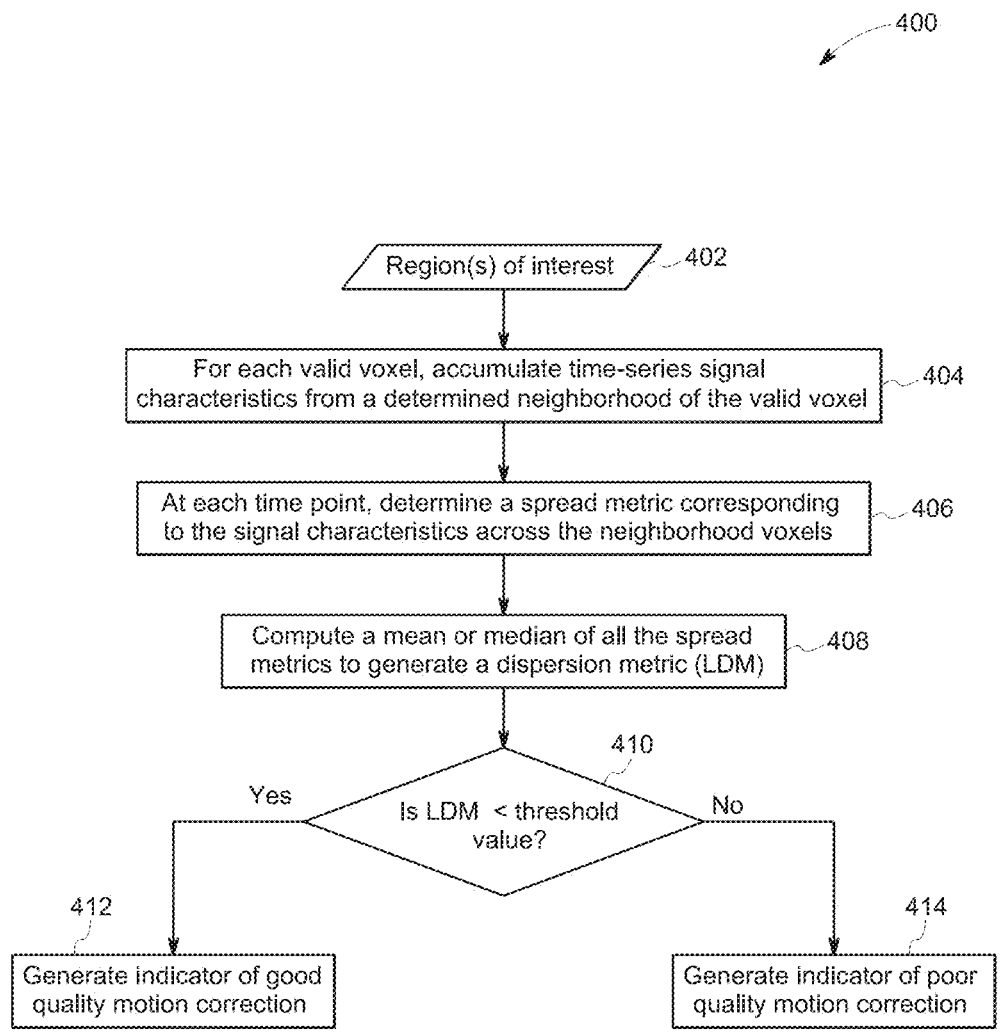
FIG. 4 is a flow chart depicting an exemplary method for determining a local dispersion metric, in accordance with aspects of the present specification.

Turning now to FIG. 4, a flowchart 400 depicting a method for computing a local dispersion metric (LDM) using the acquired images is presented. The method of FIG. 4 is described in terms of the various components of FIGS. 1-2. As previously noted, valid voxels in corresponding regions of interest 402 in the images are identified (see step 210 of FIG. 2). To facilitate the computation of the LDM, signal data curves or characteristics corresponding to the valid voxels in a determined 3D neighborhood may be stacked along rows, as indicated by step 404. In one example, the determined 3D neighborhood may include a 3×3×3 region surrounding a given valid voxel.

Subsequently, at each time point (t), a dispersion metric that is representative of dispersion of the signal data across neighborhood voxels may be determined, as depicted by step 406. In one embodiment, the dispersion metric may include a variance ($\sigma_t^2$) in the signal data at each time point. However, in other embodiments other dispersion metrics such as a Z-score, a Chi-square statistic, and the like may also be used.

Once the dispersion metric at each time point is computed, a local dispersion metric may be computed, as depicted by step 408. In one example, the LDM may be computed using the dispersion metrics corresponding to the different time points based on equation (3).

$$LDM = \sqrt{\frac{1}{Nt}\sum_{t=1}^{Nt} \sigma_t^2}. \qquad (3)$$

where $\sigma_t^2$ is representative of a variance in the signal data at a given time point t and in a given spatial neighborhood.

A lower value of the LDM is generally indicative of better alignment of the signal data at different time points in the given ROI, while a higher value of the LDM is generally indicative of poor alignment of the signal data at different time points in the given ROI. Accordingly, at step 410, the LDM value may be compared with a threshold dispersion value. The threshold dispersion values may be externally supplied based on the tissue type of the given ROI. Alternatively, the threshold dispersion values may be automatically assigned by the system 100.

At step 410, if it is verified that the LDM value is lower than the threshold dispersion value, then it may be inferred that the motion correction is of "good" quality. However, at step 410, if it is determined that the LDM value is greater than the threshold dispersion value, then it may be deduced that the quality of motion correction is "poor." Furthermore, indicators that quantify the efficacy of motion correction may be generated and overlaid on the image(s) and/or maps, as indicated by steps 412 and 414. In certain embodiments, the quantitative indicators may include shaped indicators, text, numerals, or combinations thereof. However, in other embodiments, the evaluation of the fidelity of motion correction may be indicated via use of different colors, where each color is indicative of a certain quality of motion correction.

Figure 5:
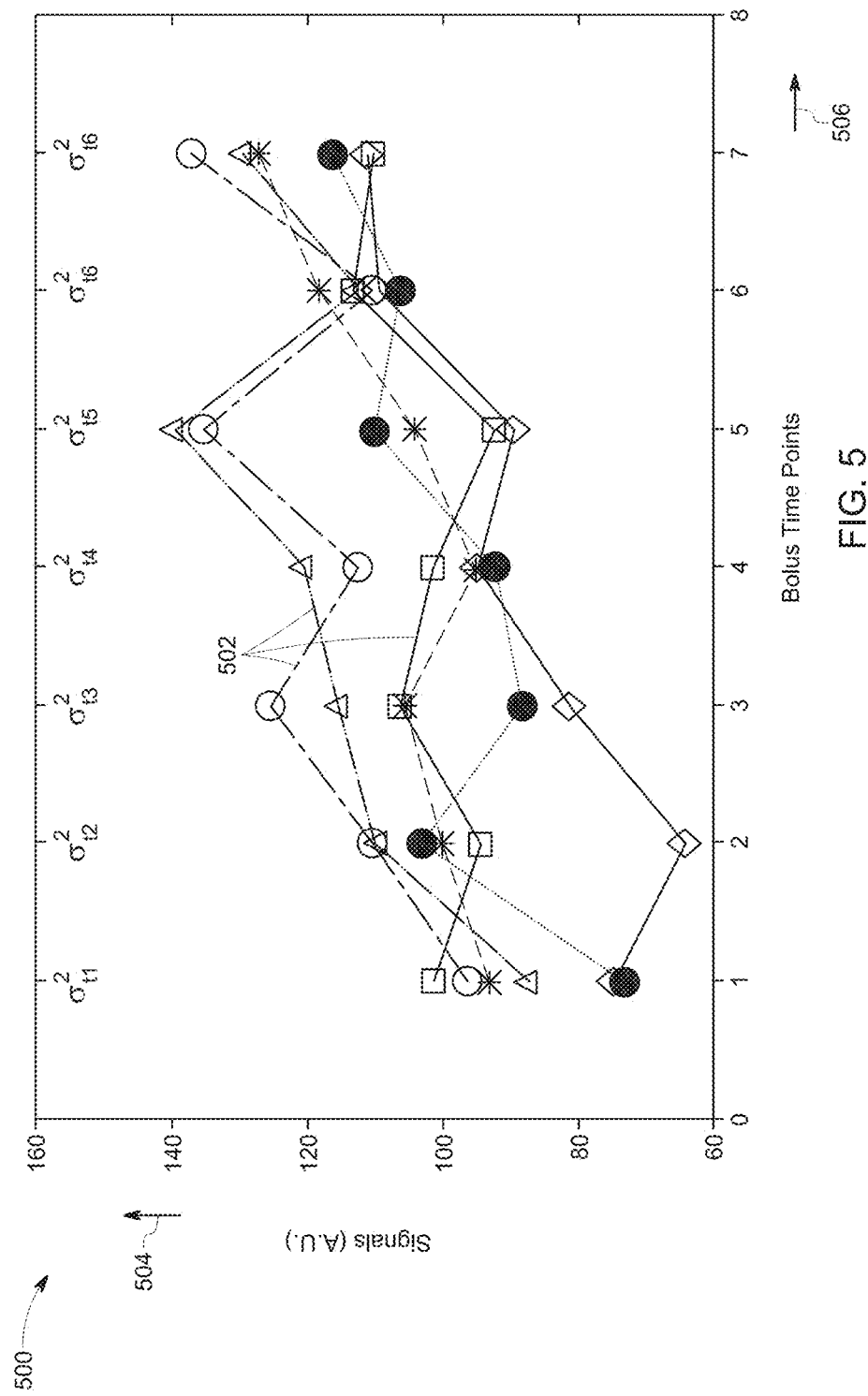
FIG. 5 is a diagrammatical representation of the exemplary method for determining the local dispersion metric of FIG. 4, in accordance with aspects of the present specification.

FIG. 5 is a diagrammatical representation 500 of the method of determining the LDM of FIG. 4. As depicted in FIG. 5, signal data curves 502 corresponding to valid voxels in a neighborhood of a valid voxel are stacked in rows. Reference numeral 504 is representative of the signal data, while bolus time points are represented by reference numeral 506.

As described with reference to FIG. 4, at each time point $t_n$, a dispersion metric that is indicative of a dispersion or spread of the signal data at that time point is computed. In the example of FIG. 5, the dispersion metric includes a variance. Accordingly, $\sigma_1^2$ is indicative of the dispersion of the signal data at time point $t_1$. In a similar fashion, dispersion metrics corresponding to time points $t_2$, $t_3$, $t_4$, $t_5$, $t_6$ and $t_7$ may be computed. Subsequently, a local dispersion metric LDM corresponding to the given ROI may be computed as indicated by equation (4).

$$LDM = \sqrt{\frac{1}{N7}\sum_{t=1}^{N7} \sigma_t^2}. \qquad (4)$$

The LDM value may then be compared with a threshold dispersion value corresponding to the label of the given ROI to assess the fidelity of the motion correction. This process may be repeated for all the ROIs in the anatomical region being imaged. Additionally, indicators that quantify the efficacy of the motion correction may be generated and displayed on or around the image and/or the dispersion map.

Figures 6C, 6D:
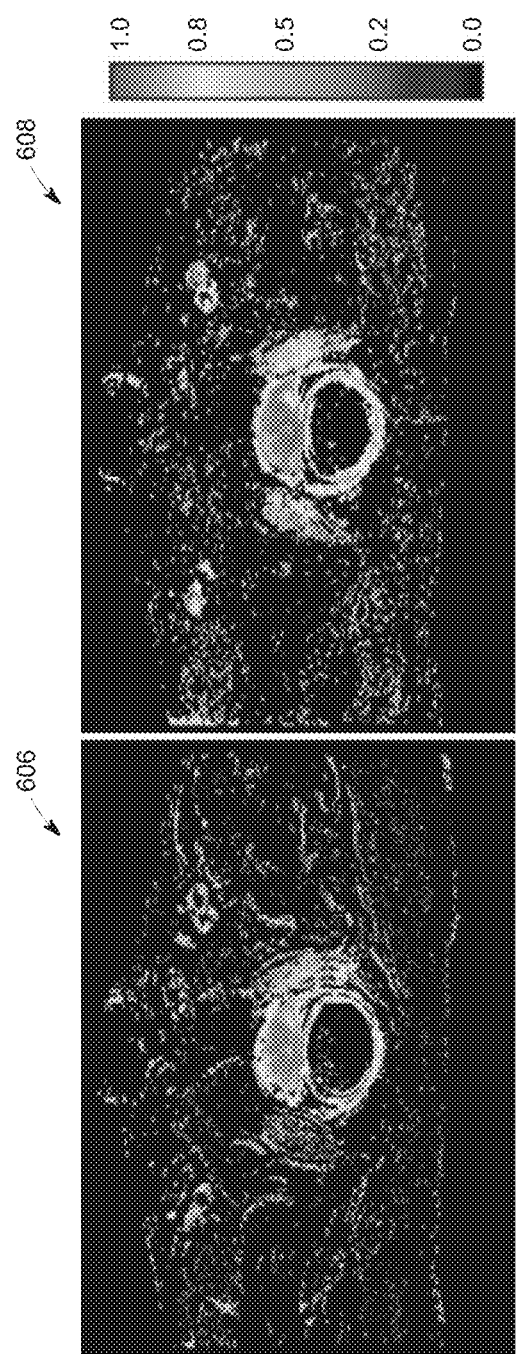

Turning now to FIGS. 6(a)-6(h), diagrammatical representations of the method of automatically evaluating the efficacy of motion correction of FIG. 2 are presented. In this example, image data corresponds to the prostrate region of a patient, such as the patient 102 (see FIG. 1). FIG. 6(a) is representative of an original image 602 corresponding to the prostrate region acquired at time point t=0 seconds. Also, FIG. 6(b) is representative of a motion corrected image 604 corresponding to an image acquired at time t=225 seconds. It may be noted that a combination of an affine transform (for example, a MI metric) and a level-set optic flow non-rigid correction (for example, a sum-of-squares error metric) are employed to correct rigid and non-rigid motion in the image data of the image 602 to generate the motion corrected image data of image 604.

As depicted in FIG. 6(a), significant motion in the prostate DCE-MRI data may be observed. The detected motion is suitably corrected by the motion correction algorithm as depicted in FIG. 6(b). The improvement in the signal data due to motion correction is captured in the maps corresponding to the LCM and LDM metrics (see FIGS. 6(c)-6(f)).

Referring now to FIG. 6(c), a diagrammatical representation 606 of an LCM map corresponding to the motion corrupted data 602 of FIG. 6(a) is presented. FIG. 6(d) is representative of an LCM map 608 corresponding to the motion corrected data of FIG. 6(b). From FIGS. 6(c)-6(d), it may be observed that the LCM metric corresponding to motion corrected image data of FIG. 6(b) is very homogenous in the region of the femoral artery and tissue surrounding prostate gland, when compared to the LCM metric corresponding to original motion corrupted image data of FIG. 6(a). Furthermore, as depicted in FIG. 6(d), the higher quality of alignment of the motion corrected data results in higher LCM values throughout the prostate field of view (FOV), post motion correction.

Figures 6E, 6F:
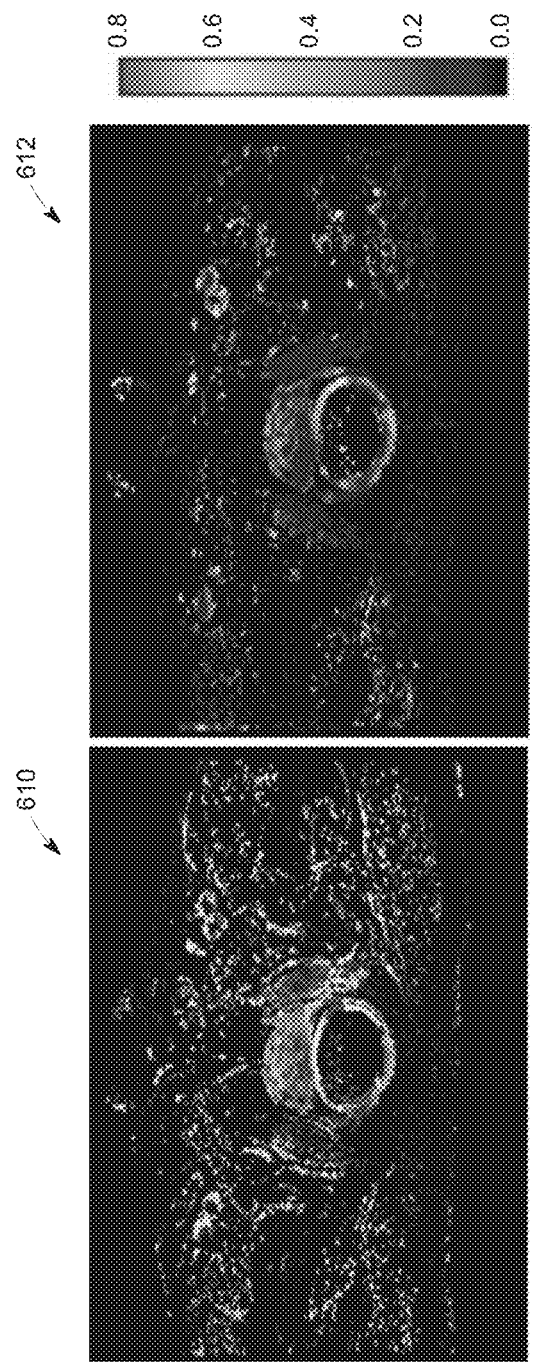

In a similar fashion, FIG. 6(e) is a diagrammatical representation 610 of an LDM map corresponding to the motion corrupted data 602 of FIG. 6(a). Also, FIG. 6(f) is a diagrammatical representation 612 of an LDM map corresponding to the motion corrected data 604 of FIG. 6(b). From FIGS. 6(f)-6(g), it may be observed that the LDM metric corresponding to motion corrected image data of FIG. 6(b) is very homogenous, when compared to the LDM metric corresponding to the original motion corrupted data of FIG. 6(a). In addition, as depicted in FIG. 6(f), the higher quality of alignment of the motion corrected data results in lower LDM values throughout the prostrate FOV, post motion correction.

Figure 6H:
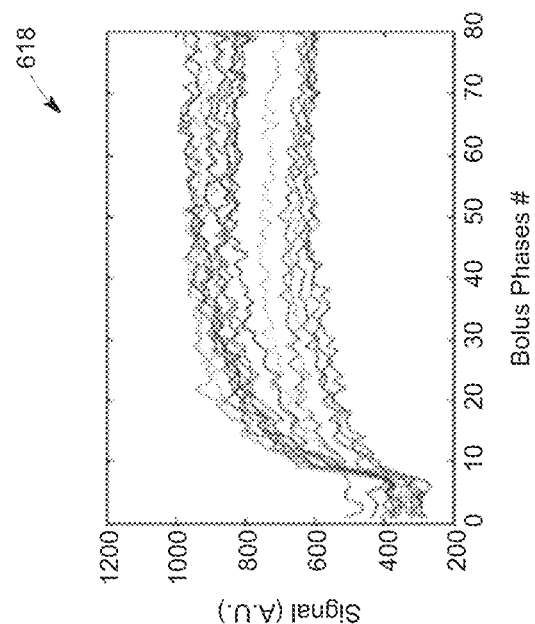
Figure 6G:
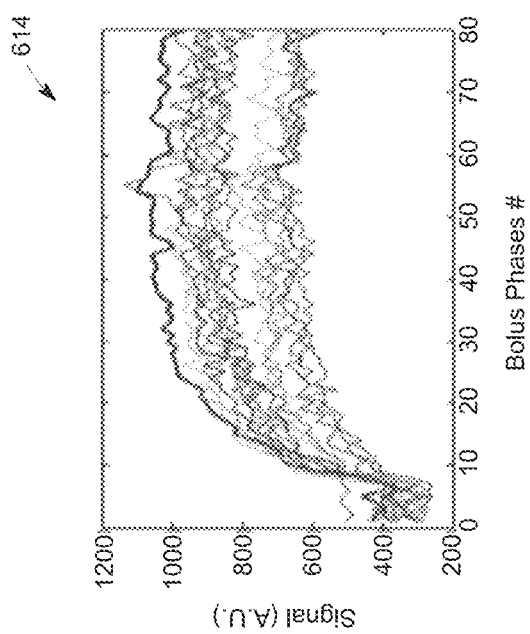

Moreover, FIG. 6(g) is a diagrammatical representation 614 of signal characteristics corresponding to a region 616 in FIG. 6(a). Also, FIG. 6(h) is a diagrammatical representation 618 of signal characteristics corresponding to a region 620 in the motion corrected image of FIG. 6(b), where the region 620 corresponds to the region 616 in the motion corrupted image of FIG. 6(a). As depicted in FIG. 6(g), there is a spread in the signal characteristics corresponding to the region 616. Referring now to FIG. 6(h), the spread in the signal characteristics corresponding to the region 620 in the motion corrected image is minimized, thereby signifying a "good" quality of motion correction.

Turning now to FIGS. 7(a)-7(g), another example of the method of automatically evaluating the efficacy of motion correction of FIG. 2 is presented. In FIG. 7(a), a diagrammatical representation 702 of an acquired image representative of a breast is depicted. In particular, this image 702 is representative of motion corrupted image data, prior to any motion correction. FIG. 7(b) depicts a diagrammatical representation 704 of a motion corrected image corresponding to the image 702 of FIG. 7(a). It may be noted that a combination of an affine transform (for example, a MI metric) and $3^{rd}$ order B-splines based non-rigid correction (for example, a MI metric) are employed to correct rigid and non-rigid motion in the image 702 to generate the motion corrected image data of image 704.

As may be observed in FIG. 7(a), there is significant motion in the breast DCE-MRI data, which is suitably corrected by a motion correction algorithm (see FIG. 7(b)). Also, FIG. 7(c) depicts a diagrammatical representation 706 of a difference image of the original image 702 and the motion corrected image 704. From the image 706 it may be observed that motion correction results in a change in at least in regions marked by arrows 708.

The improvement in the signal data due to motion correction is captured in the maps corresponding to the LCM and LDM metrics (see FIGS. 7(d)-7(g)). Referring now to FIG. 7(d), a diagrammatical representation 710 of an LCM map corresponding to the motion corrupted data 702 of FIG. 7(a) is presented. Furthermore, FIG. 7(e) is representative of an LCM map 712 corresponding to the motion corrected data of FIG. 7(b). From FIGS. 7(d)-7(e), it may be observed that the LCM metric corresponding to the motion corrected image data of FIG. 7(b) is very homogenous in the regions indicated by the arrows 708 of FIG. 7(c), when compared to the LCM metric corresponding to the original motion corrupted data of FIG. 7(a). Furthermore, as depicted in FIG. 7(e), the higher quality of alignment of motion corrected data results in higher LCM values throughout the breast FOV, post motion correction.

In a similar fashion, FIG. 7(f) is a diagrammatical representation 714 of an LDM map corresponding to the motion corrupted data 702 of FIG. 7(a). Also, FIG. 7(g) is a diagrammatical representation 716 of an LDM map corresponding to the motion corrected data 704 of FIG. 7(b). From FIGS. 7(f)-7(g), it may be noted that the LDM metric corresponding to the motion corrected image data of FIG. 7(b) is very homogenous in the region indicated by the arrows 708 of FIG. 7(c), when compared to the LDM metric corresponding to the original motion corrupted data of FIG. 7(a). Moreover, as depicted in FIG. 7(g), the higher quality of alignment of motion corrected data results in lower LDM values throughout the breast FOV, post motion correction.

The similarity metric such as the LCM primarily reflects temporal continuity in the given ROI, while the dispersion metric such as the LDM captures the spatial continuity in that ROI. The LCM and LDM maps are thus complementary and may be used in synchrony for a quantitative judgment of the motion correction. More particularly, the LCM and LDM maps may be used as a standardized mechanism for reporting improvement in dynamic data after motion correction and allow easy comparison of performance of different algorithms or site data. Also, use of normalized data in the computation of the LCM and the LDM enhances the computation of metrics. Additionally, use of tissue classification and confining the neighborhood for the computation of the LCM and LDM to different ROIs corresponding to the different tissue types also enhances the assessment of the efficacy of the motion correction.

In accordance with aspects of the present specification, the similarity metric (LCM) and the dispersion metric (LDM) are used in tandem to appropriately reflect any improvement in the alignment of dynamic 4D MRI data post registration. These metrics may also be used as a part of a motion correction workflow for quickly assessing the degree of improvement in dynamic data post motion correction. Accordingly, the LCM and LDM metrics aid in quantifying the efficacy of motion correction schemes in dynamic data across different anatomies and clinical sites.

As previously noted with reference to FIG. 1, the medical imaging system 106 may include a magnetic resonance imaging (MRI) imaging system. FIG. 800 is a block diagram of an embodiment of an MRI system 800. The MRI system 8MRI system 800 is illustrated diagrammatically as including a scanner 802, scanner control circuitry 804, and system control circuitry 806. While the MRI system 800 may include any suitable MRI scanner or detector, in the illustrated embodiment the system includes a full body scanner including a patient bore 808 into which a table 810 may be positioned to place a patient 812, such as the patient 102 in a desired position for scanning. The scanner 802 may be of any suitable type of rating, including scanners varying from 0.5 Tesla ratings to 3 Tesla ratings and beyond.

Additionally, the scanner 802 may include a series of associated coils for producing controlled magnetic fields, for generating radio-frequency (RF) excitation pulses, and for detecting emissions from gyromagnetic material within the patient 812 in response to such pulses. In the diagrammatical view of FIG. 8, a primary magnet coil 814 may be provided for generating a primary magnetic field generally aligned with patient bore 808. A series of gradient coils 816, 818 and 820 may be grouped in a coil assembly for generating controlled magnetic gradient fields during examination sequences as will be described in greater detail hereinafter. A RF coil 822 may be provided for generating radio frequency pulses for exciting the gyromagnetic material. In the embodiment illustrated in FIG. 8, the coil 822 also serves as a receiving coil. Thus, the RF coil 822 may be coupled with driving and receiving circuitry in passive and active modes for receiving emissions from the gyromagnetic material and for applying RF excitation pulses, respectively. Alternatively, various configurations of receiving coils may be provided separate from the RF coil 822. Such coils may include structures specifically adapted for target anatomies, such as head coil assemblies, and so forth. Moreover, receiving coils may be provided in any suitable physical configuration, including phased array coils, and so forth.

In a presently contemplated configuration, the gradient coils 816, 818 and 820 may have different physical configurations adapted to their function in the imaging system 800. As will be appreciated by those skilled in the art, the coils include conductive wires, bars or plates that are wound or cut to form a coil structure that generates a gradient field upon application of control pulses as described below. The placement of the coils within the gradient coil assembly may be done in several different orders. In one embodiment, a Z-axis coil may be positioned at an innermost location, and may be formed generally as a solenoid-like structure that has relatively little impact on the RF magnetic field. Thus, in the illustrated embodiment, the gradient coil 820 is the Z-axis solenoid coil, while the coils 816 and 818 are Y-axis and X-axis coils respectively.

The coils of the scanner 802 may be controlled by external circuitry to generate desired fields and pulses, and to read signals from the gyromagnetic material in a controlled manner. As will be appreciated by those skilled in the art, when the material, typically bound in tissues of the patient, is subjected to the primary field, individual magnetic moments of the paramagnetic nuclei in the tissue partially align with the field. While a net magnetic moment is produced in the direction of the polarizing field, the randomly oriented components of the moment in a perpendicular plane generally cancel one another. During an examination sequence, an RF frequency pulse is generated at or near the Larmor frequency of the material of interest, resulting in rotation of the net aligned moment to produce a net transverse magnetic moment. This transverse magnetic moment precesses around the main magnetic field direction, emitting RF signals that are detected by the scanner 802 and processed for reconstruction of the desired image.

The gradient coils 816, 818 and 820 may be configured to serve to generate precisely controlled magnetic fields, the strength of which vary over a predefined field of view, typically with positive and negative polarity. When each coil is energized with known electric current, the resulting magnetic field gradient is superimposed over the primary field and produces a desirably linear variation in the Z-axis component of the magnetic field strength across the field of view. The field varies linearly in one direction, but is homogenous in the other two. The three coils have mutually orthogonal axes for the direction of their variation, enabling a linear field gradient to be imposed in an arbitrary direction with an appropriate combination of the three gradient coils.

The pulsed gradient fields perform various functions integral to the imaging process. Some of these functions are slice selection, frequency encoding and phase encoding. These functions may be applied along the X-axis, Y-axis and Z-axis of the original coordinate system or along other axes determined by combinations of pulsed currents applied to the individual field coils.

The slice select gradient determines a slab of tissue or anatomy to be imaged in the patient. The slice select gradient field may be applied simultaneously with a frequency selective RF pulse to excite a known volume of spins within a desired slice that precess at the same frequency. The slice thickness is determined by the bandwidth of the RF pulse and the gradient strength across the field of view.

The frequency encoding gradient is also known as the readout gradient, and is usually applied in a direction perpendicular to the slice select gradient. In general, the frequency encoding gradient is applied before and during the formation of the magnetic resonance (MR) echo signal resulting from the RF excitation. Spins of the gyromagnetic material under the influence of this gradient are frequency encoded according to their spatial position along the gradient field. By Fourier transformation, acquired signals may be analyzed to identify their location in the selected slice by virtue of the frequency encoding.

The phase encode gradient is generally applied before the readout gradient and after the slice select gradient. Localization of spins in the gyromagnetic material in the phase encode direction may be accomplished by sequentially inducing variations in phase of the precessing protons of the material using slightly different gradient amplitudes that are sequentially applied during the data acquisition sequence. The phase encode gradient permits phase differences to be created among the spins of the material in accordance with their position in the phase encode direction.

As will be appreciated by those skilled in the art, a great number of variations may be devised for pulse sequences employing the exemplary gradient pulse functions described hereinabove as well as other gradient pulse functions not explicitly described here. Moreover, adaptations in the pulse sequences may be made to appropriately orient both the selected slice and the frequency and phase encoding to excite the desired material and to acquire resulting MR signals for processing.

The coils of the scanner 802 are controlled by scanner control circuitry 804 to generate the desired magnetic field and RF pulses. In the diagrammatical view of FIG. 8, the control circuitry 804 thus includes a control circuit 826 for commanding the pulse sequences employed during the examinations, and for processing received signals. The control circuit 826 may include any suitable programmable logic device, such as a CPU or digital signal processor of a general purpose or application-specific computer. Also, the control circuit 826 may further include memory circuitry 828, such as volatile and non-volatile memory devices for storing physical and logical axis configuration parameters, examination pulse sequence descriptions, acquired image data, programming routines, and so forth, used during the examination sequences implemented by the scanner.

Interface between the control circuit 826 and the coils of the scanner 802 is managed by amplification and control circuitry 830 and by transmission and receive interface circuitry 832. The amplification and control circuitry 830 includes amplifiers for each gradient field coil to supply drive current to the field coils in response to control signals from control circuit 826. Transmit/receive (T/R) circuitry 832 includes additional amplification circuitry for driving the RF coil 822. Moreover, where the RF coil 822 serves both to emit the RF excitation pulses and to receive MR signals, the T/R circuitry 832 may typically include a switching device for toggling the RF coil between active or transmitting mode, and passive or receiving mode. A power supply, denoted generally by reference numeral 824 in FIG. 8, is provided for energizing the primary magnet 814. Finally, the scanner control circuitry 804 may include interface components 834 for exchanging configuration and image data with system control circuitry 806. It should be noted that, while in the present description reference is made to a horizontal cylindrical bore imaging system employing a superconducting primary field magnet assembly, the present technique may be applied to various other configurations, such as scanners employing vertical fields generated by superconducting magnets, permanent magnets, electromagnets or combinations of these means.

The system control circuitry 806 may include a wide range of devices for facilitating interface between an operator or radiologist and the scanner 802 via the scanner control circuitry 804. In the illustrated embodiment, for example, an operator controller 836 is provided in the form of a computer workstation employing a general purpose or application-specific computer. The workstation also typically includes memory circuitry for storing examination pulse sequence descriptions, examination protocols, user and patient data, image data, both raw and processed, and so forth. Further, the workstation may further include various interface and peripheral drivers for receiving and exchanging data with local and remote devices. In the illustrated embodiment, such devices include a conventional computer keyboard 840 and an alternative input device such as a mouse 842. A printer 844 may be provided for generating hard copy output of documents and images reconstructed from the acquired data. Moreover, a computer monitor 838 may be provided for facilitating operator interface. In addition, the system 800 may include various local and remote image access and examination control devices, represented generally by reference numeral 846 in FIG. 8. Such devices may include picture archiving and communication systems, teleradiology systems, and the like.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the invention. Thus, those skilled in the art will appreciate that the present MRI system 800 is provided by way of example, and the present specification is in no way limited by the specific system configuration.

In the example of FIG. 8, an exemplary evaluating platform 848 such as the evaluating platform 112 of FIG. 1 is shown as being operatively coupled to the MRI system 800. However, in certain other embodiments, the motion detecting platform 848 may be an integral part of the MRI system 800.

Furthermore, the foregoing examples, demonstrations, and process steps such as those that may be performed by the system may be implemented by suitable code on a processor-based system, such as a general-purpose or special-purpose computer. It should also be noted that different implementations of the present specification may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may include paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

The various systems and methods for automated evaluation of the efficacy of motion correction presented hereinabove provide a framework for robust assessment of fidelity of the motion correction. Additionally, the framework enables the robust quantification of the motion correction. Moreover, since the systems and methods allow speedy appraisal of the efficacy of the motion correction, this information may be used to enhance the clinical workflow. Furthermore, the systems and methods presented herein allow the automated evaluation of the fidelity of motion correction, which in turn enhances the image data acquisition, while minimizing net scan time for the clinician, and thereby improving clinical workflow.

Also, local correlation and dispersion based metrics are employed to dependably reflect the improvement in dynamic 3D and/or 4D MRI data alignment post motion correction. These metrics may be used as part of motion correction workflow for quickly assessing the degree of improvement in dynamic data post correction. The metrics also provide means for quantifying the efficacy of motion correction schemes in dynamic data across different anatomies and clinical sites.

Determination of motion of organs such as the breast, the prostrate, bones, the kidneys, the lungs, the uterus, and the like is generally challenging. In addition, flow of contrast exacerbates the problem, thereby making it difficult for techniques such as difference images or visual techniques to assess the fidelity of motion correction. The systems and methods described hereinabove circumvent the shortcomings of the presently available techniques and aid in the automated evaluation of efficacy of motion correction in in 3D and/or 4D DCE-MRI, DSC-MRI or DCE-CT scans of the organs.

Additionally, the systems and methods provide an enhanced clinical workflow for allowing the clinicians to assess the efficacy of motion correction in dynamic time-series data. Moreover, the acquired 4D image data is used to demonstrate fidelity of motion correction, thereby circumventing the need for additional data or steps. Furthermore, the systems and methods presented hereinabove allow the clinicians to understand the robustness of motion correction as part of motion correction workflow.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

We claim:

1. A method for automated evaluation of motion correction, the method comprising:
   identifying one or more regions of interest in each of a plurality of images corresponding to a subject of interest;
   selecting valid voxels in each of the one or more regions of interest in each of the plurality of images;
   computing a similarity metric, a dispersion metric, or both the similarity metric and the dispersion metric for each region of interest in each of the plurality of images, wherein the similarity metric includes a local correlation metric computed as a correlation of the valid voxels with their neighboring voxels; and
   generating a similarity map, a dispersion map, or both the similarity map and the dispersion map based on at least one of the similarity metrics and the dispersion metrics corresponding to the one or more regions of interest.

2. The method of claim 1, wherein computing a similarity, a dispersion metric, or both further comprises computing the dispersion metric for each region of interest in each of the plurality of images.

3. The method of claim 2, wherein the plurality of images comprises motion corrupted dynamic contrast images.

4. The method of claim 2, wherein the plurality of images comprises motion corrected dynamic contrast images.

5. The method of claim 4, further comprising using a contrast agent, wherein the contrast agent comprises an endogenous contrast agent, an exogenous contrast agent, or a combination thereof.

6. The method of claim 5, wherein obtaining the plurality of images comprises acquiring one or more images prior to administering the contrast agent to the patient.

7. The method of claim 6, wherein obtaining the plurality of images further comprises acquiring one or more images after administering the contrast agent to the patient.

8. The method of claim 1, wherein identifying the one or more regions of interest in each of the plurality of images comprises:
ascertaining one or more tissue types in an anatomical region in the subject of interest; and
labeling the one or more tissue types to identify the one or more regions of interest.

9. The method of claim 1, wherein selecting the valid voxels in each of the one or more regions of interest in each of the plurality of images comprises:
normalizing signal characteristics corresponding to each of the one or more regions of interest in each of the plurality of images;
categorizing voxels as the valid voxels based on a determined threshold; and
classifying voxels as noise voxels based on the determined threshold.

10. The method of claim 9, wherein the signal characteristics comprise a signal modulated by a contrast flow.

11. The method of claim 1, wherein computing the similarity metric for each valid voxel in each region of interest comprises:
accumulating time series signal characteristics corresponding to valid voxels in a determined neighborhood of each valid voxel;
computing a correlation metric for each valid voxel based on the time series signal characteristics corresponding to the valid voxels in the determined neighborhood; and
determining a mean or a median of the correlation metrics corresponding to the valid voxels in each region of interest to generate the similarity metric.

12. The method of claim 11, further comprising comparing the similarity metric to a threshold value corresponding to each region of interest to determine an efficacy of motion correction.

13. The method of claim 12, wherein generating the similarity map comprises creating the similarity map based on the similarity metric corresponding to each region of interest.

14. The method of claim 1, wherein computing the dispersion metric for each valid voxel in each region of interest comprises:
accumulating time series signal characteristics corresponding to valid voxels in a determined neighborhood of each valid voxel;
determining a spread metric of the time series signal characteristics for each valid voxel based on the signal characteristics corresponding to the valid voxels in the determined neighborhood at each time point; and
computing a mean or a median of the spread metrics corresponding to the valid voxels in each region of interest to generate the dispersion metric.

15. The method of claim 14, further comprising comparing the dispersion metric to a threshold value corresponding to each region of interest to determine an efficacy of motion correction.

16. The method of claim 14, wherein generating the dispersion map comprises creating the dispersion map based on the dispersion metric corresponding to each region of interest.

17. The method of claim 1, wherein generating the similarity map, the dispersion map, or both the similarity map and the dispersion map further comprises annotating the similarity map and the dispersion map based on the similarity metrics and the dispersion metrics corresponding to the one or more regions of interest.

18. The method of claim 1, further comprising communicating the similarity map and the dispersion map to a clinician.

19. The method of claim 18, wherein communicating the similarity map and the dispersion map to the clinician comprises visualizing one or more of the similarity map, the dispersion map, and an indicator representative of the efficacy of motion correction on a display, wherein the indicator is derived from a comparison of at least one of the similarity metric and the dispersion metric to a threshold value.

20. The method of claim 1, further comprising altering acquisition of image data based on the similarity map and the dispersion map.

21. A system for automated evaluation of motion correction, the system comprising:
a motion correction evaluating platform configured to:
identify one or more regions of interest in each of a plurality of images corresponding to a subject of interest;
select valid voxels in each of the one or more regions of interest in each of the plurality of images;
compute a similarity metric, a dispersion metric, or both the similarity metric and the dispersion metric for each region of interest in each of the plurality of images, wherein the similarity metric includes a local correlation metric computed as a correlation of the valid voxels with their neighboring voxels; and
generate a similarity map, a dispersion map, or both the similarity map and the dispersion map based on at least of the similarity metrics and the dispersion metrics corresponding to the one or more regions of interest.

22. An imaging system, comprising:
an acquisition subsystem configured to acquire image data corresponding to a subject of interest;
a processing subsystem in operative association with the acquisition subsystem and configured to process the acquired image data, wherein the processing subsystem comprises a motion correction evaluating platform configured to:
identify one or more regions of interest in each of a plurality of images corresponding to a subject of interest;
select valid voxels in each of the one or more regions of interest in each of the plurality of images;
compute a similarity metric, a dispersion metric, or both the similarity metric and the dispersion metric for each region of interest in each of the plurality of images, wherein the similarity metric includes a local correlation metric computed as correlation of the valid voxels with their neighboring voxels; and
generate a similarity map, a dispersion map, or both the similarity map and the dispersion map based on at least one of the similarity metrics and the dispersion metrics corresponding to the one or more regions of interest.

23. The imaging system of claim 22, wherein the imaging system is a magnetic resonance imaging system, an ultrasound imaging system, a contrast enhanced ultrasound imaging system, an optical imaging system, an X-ray imaging system, a computed tomography imaging system, a positron emission tomography imaging system, or combinations thereof.

* * * * *